United States Patent [19]

Wietek

[11] Patent Number: 5,403,550
[45] Date of Patent: Apr. 4, 1995

[54] ELECTRODE FOR DETERMINING THE STATE OF CORROSION OF METAL RENFORCEMENT IN CONCRETE CONSTRUCTIONS

[76] Inventor: Bernhard Wietek, No. 290, A-6073 Sistrans, Austria

[21] Appl. No.: 137,064
[22] PCT Filed: Dec. 14, 1992
[86] PCT No.: PCT/AT92/00167
  § 371 Date: Oct. 21, 1993
  § 102(e) Date: Oct. 21, 1993
[87] PCT Pub. No.: WO93/17323
  PCT Pub. Date: Sep. 2, 1993

[30] Foreign Application Priority Data

Feb. 21, 1992 [AT] Austria ............... 321/92
Nov. 20, 1992 [AT] Austria ............... 2307/92

[51] Int. Cl.⁶ .............. G01N 17/04; G01N 17/02; G01N 27/26
[52] U.S. Cl. .............. 422/53; 204/404; 324/700; 436/6
[58] Field of Search ........... 204/404; 324/700; 422/53; 436/6; 174/121 R, 121 SR

[56] References Cited

U.S. PATENT DOCUMENTS

| | | | |
|---|---|---|---|
| 2,298,324 | 10/1942 | Williams | 174/121 SR X |
| 2,851,570 | 9/1958 | Schaschl | 324/700 |
| 3,209,249 | 9/1965 | Warfield | 324/703 |
| 3,236,096 | 2/1966 | Macatician et al. | 324/700 X |
| 3,599,090 | 8/1971 | Fitzpatrick et al. | 422/53 X |
| 4,255,241 | 3/1981 | Kroon et al. | 204/147 |
| 4,703,253 | 10/1987 | Strommen | 324/700 |
| 4,703,255 | 10/1987 | Strommen | 324/700 |
| 4,758,324 | 7/1988 | Winneti et al. | 204/404 |
| 4,942,354 | 7/1990 | Miller | 204/404 X |
| 4,957,612 | 9/1990 | Stewart et al. | 204/196 |
| 5,015,355 | 5/1991 | Schiessel | 204/404 |

FOREIGN PATENT DOCUMENTS

72398 4/1970 Denmark .
2169410 7/1986 United Kingdom .

OTHER PUBLICATIONS

Gjoerv, O. et al. *Chem. Abstr.* 1979 90, 159127b.
O. E. Gjorv et al. *Mater. Perform.*, 1982 21, 33–35.
O. Gjoerv et al., *Chem. Abstr.* 1982 96, 112282g.
R. Stroemmen *Chem. Abstr.* 1989, 110, 123814v.

*Primary Examiner*—James C. Housel
*Assistant Examiner*—Arlen Soderquist
*Attorney, Agent, or Firm*—Wenderoth, Lind & Ponack

[57] ABSTRACT

An electrode for determining corrosion of metal reinforcement in concrete includes a wire surrounded by insulation and made of a metal which is more electropositive than a metal reinforcement. An electrically active part of the wire is in electrolytic contact with moisture in concrete surrounding the reinforcement. The insulation is disposed along the whole of the electrically active part of the wire in such a way that the insulation keeps this part of the wire separated from the reinforcement and galvanically insulated therefrom.

4 Claims, 2 Drawing Sheets

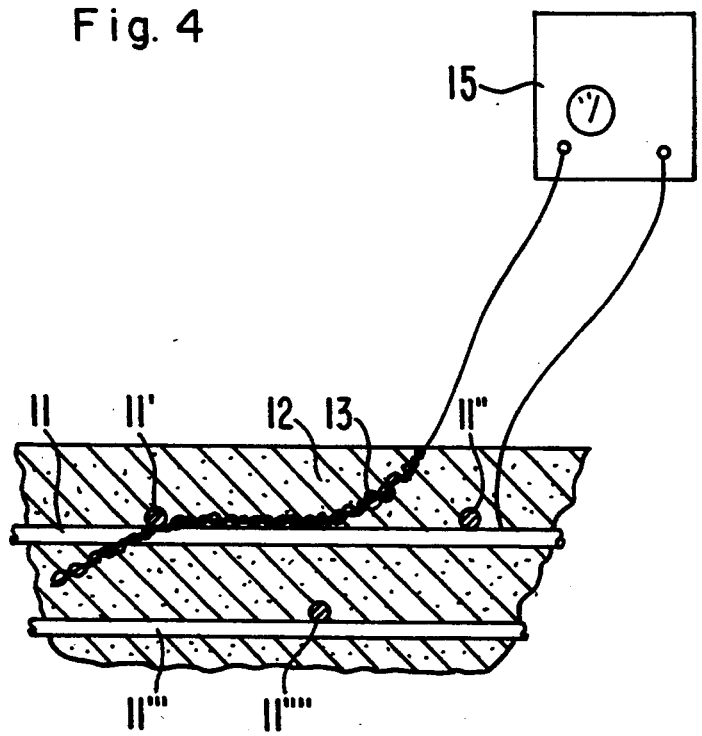

ELECTRODE FOR DETERMINING THE STATE OF CORROSION OF METAL RENFORCEMENT IN CONCRETE CONSTRUCTIONS

BACKGROUND OF THE INVENTION

The present invention relates to an electrode for determining the state of corrosion of metal reinforcement in concrete constructions, this being in the form of a wire that is more electro-positive than the reinforcement metal and that is surrounded by insulation. The electrically active part of the wire is in electrolytic contact with the moisture in the concrete.

In principle, corrosion protection for the reinforcement in concrete constructions is produced by the high alkalinity of the concrete, because of which a rust-inhibiting passive layer forms on the surfaces of the reinforcement steel. Despite this, in recent years, damage caused by corrosion has been identified in reinforced steel constructions, mainly in communications (road) infrastucture such as bridges, this having been caused predominantly by the effects of salt. Apart from the effects of salt, the passive layer on the surface of the steel can also be destroyed because the concrete reacts with the carbon dioxide in the surrounding air and thus loses its alkalinity by the formation of carbonates.

The potential on the boundary layer between the steel and the concrete can be measured with the help of electrodes. In time, a constant potential that corresponds to the passivated state of the reinforcement (area of passivity) is formed on the reinforcement, manufactured and installed in the normal way, which has undamaged corrosion protection. If there is a change in the state of the cement mortar, which can lead to corrosion, it will be possible to identify a reduction of the potential. This reduction is particularly great in the case of reinforcement steel in which there are places that are corroding.

An even more reliable estimate of the probability of corrosion can be achieved by measurement of the potential after anodic polarization. A brief anodic galvanostatic DC pulse is applied to the reinforcement steel through one of the measurement electrodes, and the resulting change in potential is measured. In a zone that is free of corrosion, there will be a greater change in potential than is found in a zone with areas of corrosion.

DD 72398 describes an electrode of the type described heretofore, in which the electrically active area lies uncovered in the concrete and only the connecting wire that leads outwardly therefrom is enclosed by continuous insulation. However, it is difficult to incorporate the secondary electrode that is used in the measurement process parallel and at a defined distance from the reinforcement steel, as is described in DD 72398. Even in the case of subsequently tightened wire anchors it is difficult to avoid metallic contact between the electrodes and the reinforcement steel with any degree of certainty. Of course, point contact between the electrodes and the reinforcement steel or extreme closeness of these two elements, which could falsify the results obtained, would be cause for concern if it was desired to install the measurement electrode in the concrete together with any reinforcement steel.

SUMMARY OF THE INVENTION

It is the task of the present invention to extend the area of application of electrical monitoring of state of corrosion of reinforcement steel whereby monitoring electrodes are installed in any reinforced construction without any particular demands for the precision with which they are positioned.

According to the present invention, in order to solve this problem, it is proposed that insulation be so arranged along the total electrically active area of a wire of the electrode that it keeps this area at a distance therefrom reinforcement and is galvanically insulated from this.

The electrical properties of the material used for the insulation should as nearly as possible be identical to those of the concrete, for which reason, it would be quite possible to surround the wire with small concrete bodies before it is installed in the concrete. However, for reasons of easier production and mechanical strength, it is recommended that another material be used, which is similarly non-conductive but which can be permeated by the moisture in the concrete that acts as electrolyte. Clay that is fired at relatively low temperatures (for example 850° C.) in order to retain its porosity, is particularly suitable. Cardboard also displays the necessary electrical properties.

The insulating bodies that are used should, as far as possible, be chemically neutral; in any case, their inherent electro-chemical activity should not falsify measurement results.

If the electrical properties of the insulating bodies differ only insignificantly from those of concrete, they will, for all practical purposes, have no influence on the results of measurement. However, a slight systematic influence by the insulating bodies will do no harm, because corrosion monitoring is not based on the absolute value of the potential that is measured, but rather on changes of potential, which depend on the degree of corrosion.

For this reason, it is also possible to form the insulating bodies from a material that is not itself permeable to the moisture in the construction. A prerequisite is that this insulation leaves sufficiently large intervening spaces open, through which the concrete comes into direct contact with the bare wire. In an embodiment of this kind it is particularly favourable if the insulation consist of threads of insulating material, particularly of plastic, that are wound on over each other, in opposite directions.

BRIEF DESCRIPTION OF THE DRAWINGS

Other objects, features and advantages of the present invention will be apparent from the following detailed description, taken with the accompanying drawings, wherein:

FIG. 4 is a schematic partial section of a concrete structure incorporating a corrosion monitoring system according to the present invention.

DETAILED DESCRIPTION OF THE INVENTION

Figure 1:
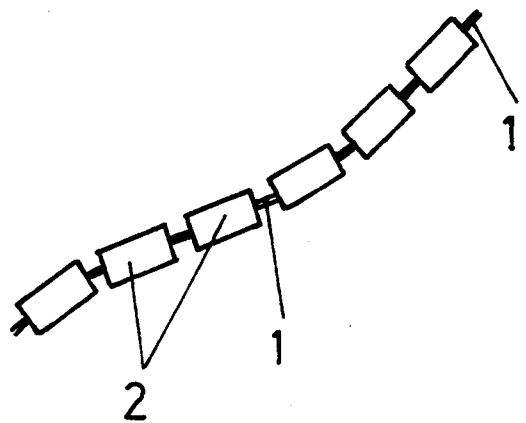
FIG. 1 is a view of an electrode employed in accordance with the present invention.
Figure 2:
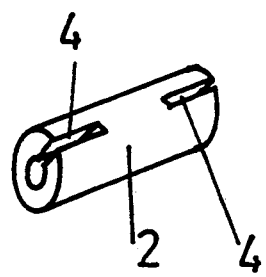
FIG. 2 is a perspective view of an insulating body of such electrode.
Figure 3:
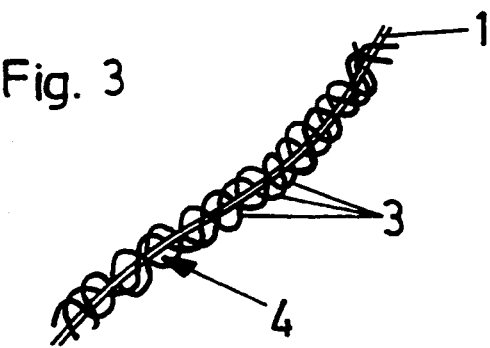
FIG. 3 is a view of a further embodiment of an electrode employable in the present invention.

Embodiments of the present invention are shown in the drawings appended hereto; FIGS. 1 to 3 relate to a total of three exemplary embodiments.

In the embodiment shown in FIG. 1, a wire 1 is surrounded by beads 2 in at least that part that is to act as an active part of an electrode within a concrete construction. Beads 2 can be in the form of balls, cylinders, or the like. The beads 2 have the smallest effect on the measurement results if they are of porous material whose properties approximate those of concrete as closely as possible.

As is shown in FIG. 2, it is also possible to make the insulating bodies that are threaded onto the wire 1 from non-permeable material, for example plastic, if sufficiently large intervening spaces 4 are provided, through which the concrete can reach the bare wire 1. Winding the wire with oppositely oriented courses of thread 3 that is of insulating material is simpler than threading bead-like insulating bodies onto the wire, as is shown in FIG. 3. The concrete can move very easily into the intervening spaces 4 between the threads 3, and the threads 3 serve as spacers relative to the reinforcement.

FIG. 4 schematically shows an electrode 13 of this kind, together with reinforcement 11-11'''' that is to be monitored and which can be, for example, a reinforcing-steel mesh or an anchor, surrounded with poured concrete 12. A device 15 for measuring potential is connected with one end of the electrode 13 from the outsides and of course, also to the reinforcement itself.

In the event that it is intended to monitor a specific part of the reinforcement, for example, an anchor, by way of the electrode, it is also possible to surround the electrode and the part of the reinforcement with common insulation, for example, a sleeve, as has already been proposed in DE-A 1-40 10 800.

I claim:

1. A corrosion monitoring system of a concrete structure including metal reinforcements embedded in concrete, said system comprising:
    an electrode embedded in said concrete, said electrode comprising a wire that is more electro-positive than said metal reinforcements, and insulation surrounding said wire and comprising threads of insulating material that are wound onto said wire over each other and in opposite directions; and
    means for measuring the electrical potential between said electrode and at least one of said metal reinforcements.

2. A system as claimed in claim 1, wherein said insulating material comprises plastic.

3. A system as claimed in claim 1, wherein said insulating material has electrical properties approximately the same as electrical properties of said concrete.

4. A system as claimed in claim 1, wherein said threads are wound onto the entire length of an electrically active part of said wire and space said wire from said metal reinforcements.

* * * * *